US007357947B2

(12) United States Patent
Nimni

(10) Patent No.: US 7,357,947 B2
(45) Date of Patent: *Apr. 15, 2008

(54) BONE GRAFT MATERIAL INCORPORATING DEMINERALIZED BONE MATRIX AND LIPIDS

(75) Inventor: Marcel E. Nimni, Santa Monica, CA (US)

(73) Assignee: Biomet, Inc., Warsaw, IN (US)

( * ) Notice: Subject to any disclaimer, the term of this patent is extended or adjusted under 35 U.S.C. 154(b) by 558 days.

This patent is subject to a terminal disclaimer.

(21) Appl. No.: 10/413,171

(22) Filed: Apr. 11, 2003

(65) Prior Publication Data
US 2004/0091459 A1 May 13, 2004

Related U.S. Application Data

(63) Continuation-in-part of application No. 09/950,264, filed on Sep. 10, 2001, now Pat. No. 6,565,884.

(51) Int. Cl.
A61K 9/14 (2006.01)
A61K 35/32 (2006.01)
A61F 2/00 (2006.01)

(52) U.S. Cl. .................. 424/484; 424/422; 424/423; 424/549

(58) Field of Classification Search ................ 424/422, 424/484, 93.9, 549
See application file for complete search history.

(56) References Cited

U.S. PATENT DOCUMENTS 4,191,747 A 3/1980 Scheicher (Continued)

FOREIGN PATENT DOCUMENTS

WO    WO 98/40113    * 9/1998

OTHER PUBLICATIONS

J.I. Irving & R.E. Wuthier, "Histochemistry and Biochemistry of Calcification with Special Reference to the Role of Lipids," *Clin. Orthoped. Rel. Res.* 56: 237-260 (1968).

(Continued)

*Primary Examiner*—Michael G. Hartley
*Assistant Examiner*—Blessing M Fubara
(74) *Attorney, Agent, or Firm*—Catalyst Law Group, APC; Michael B. Farber, Esq.

(57) ABSTRACT

One embodiment of the invention is demineralized bone putty composition comprises: (1) demineralized bone matrix (DBM); and (2) a lipid fraction selected from the group consisting of lecithin and a mixture of lecithin and triglycerides containing unsaturated fatty acids. The putty composition is moldable, biocompatible, slowly resorbable, insoluble in tissue fluids, and non-extrudable. The composition delivers a biologically active product to animals and humans that will enhance bone formation at sites where bone is lost, deficient, or present in suboptimal amounts. The composition can further comprise calcium, an antioxidant such as Vitamin E or Vitamin C, or a hydrophilic polymer such as methylcellulose, a methylcellulose derivative, carboxymethyl cellulose, or hydroxypropyl methylcellulose. A second embodiment of the invention is a demineralized bone paste composition comprising: (1) about 15% to about 75% of an emulsion carrier, such as an aqueous phase; and (2) a bone-material-containing phase comprising: (a) demineralized bone matrix (DBM); and (b) an emulsifier component that is compatible with lipids. This bone paste composition is moldable, biocompatible, slowly resorbable, miscible with bone graft materials, soluble or partially soluble in tissue fluids, and extrudable.

86 Claims, 2 Drawing Sheets

U.S. PATENT DOCUMENTS

| | | | |
|---|---|---|---|
| 4,196,218 A * | 4/1980 | Thiele | 514/560 |
| 4,394,370 A | 7/1983 | Jeffries | |
| 4,472,840 A | 9/1984 | Jeffries | |
| 4,642,120 A | 2/1987 | Nevo et al. | |
| 4,795,804 A * | 1/1989 | Urist | 530/350 |
| 4,801,299 A | 1/1989 | Brendel et al. | |
| 4,879,135 A | 11/1989 | Greco et al. | |
| 4,895,629 A * | 1/1990 | Castegnier et al. | 204/483 |
| 4,908,151 A * | 3/1990 | Inoue et al. | 252/188.28 |
| 4,946,792 A | 8/1990 | O'Leary | |
| 4,976,733 A | 12/1990 | Girardot | |
| 5,053,049 A | 10/1991 | Campbell | |
| 5,059,293 A * | 10/1991 | Sugishima et al. | 428/418 |
| 5,067,962 A | 11/1991 | Campbell et al. | |
| 5,073,373 A * | 12/1991 | O'Leary et al. | 424/422 |
| 5,229,497 A | 7/1993 | Boni | |
| 5,236,456 A | 8/1993 | O'Leary et al. | |
| 5,284,655 A | 2/1994 | Bogdansky et al. | |
| 5,290,558 A * | 3/1994 | O'Leary et al. | 424/422 |
| 5,298,254 A | 3/1994 | Prewett et al. | |
| 5,314,476 A | 5/1994 | Prewett et al. | |
| 5,405,390 A | 4/1995 | O'Leary et al. | |
| 5,439,684 A | 8/1995 | Prewett et al. | |
| 5,484,601 A | 1/1996 | O'Leary et al. | |
| 5,510,396 A | 4/1996 | Prewett et al. | |
| 5,607,476 A | 3/1997 | Prewett et al. | |
| 5,707,962 A | 1/1998 | Chen et al. | |
| 5,733,545 A | 3/1998 | Hood, III | |
| 5,919,808 A * | 7/1999 | Petrie et al. | 514/372 |
| 5,980,948 A | 11/1999 | Goedemoed et al. | |
| 6,123,731 A | 9/2000 | Boyce et al. | |
| 6,326,018 B1 * | 12/2001 | Gertzman et al. | 424/423 |
| 6,352,972 B1 | 3/2002 | Nimni et al. | |
| 6,565,884 B2 * | 5/2003 | Nimni | 424/484 |
| 7,001,611 B2 * | 2/2006 | Kiso et al. | 424/439 |
| 7,138,489 B2 * | 11/2006 | Minamitake et al. | 530/334 |

OTHER PUBLICATIONS

M.R. Urist et al., "Lipids Closely Associated with Bone Morphogenetic Protein (BMP) and Induced Heterotopic Bone Formation," *Connect Tissue Res.* 36: 9-20 (1997).

M.E. Nimni, "Polypeptide Growth Factors: Targeted Delivery Systems," *Biomaterials* 18: 1201-1225 (1997).

M.R. Urist & T.A. Dowell, "The Inductive Substratum for Osteogenesis in Pellets of Particulate Bone Matrix," *Clin. Orthoped. Rel. Res.* 61: 61-68 (1969).

M.R. Urist & B.S. Strates, "Bone Morphogenetic Protein," *J. Dent. Res.* 50: 1392-1406 (1971).

B.S. Strates & J.J. Tidman, "Contribution of Osteoinductive and Osteoconductive Properties of Demineralized Bone Matrix to Skeletal Repair," *Euro. J. Exp. Musculoskel. Res.* 2.

M.R. Urist et al., "Solubilized and Insolubilized Bone Morphogenetic Proteins," *Proc. Natl. Acad. Sci. USA* 76: 1828-1832 (1979).

C.B. Huggins et al., "Transformation of Fibroblasts by Allogeneic and Xenogeneic Transplants of Demineralized Tooth and Bone," *J. Exp. Med.* 132: 1250-1258 (1970).

A.H. Reddi & C.B. Huggins, "Influence of Transplanted Tooth and Bone on Transformation of Fibroblasts," *Proc. Soc. Exp. Biol.* 143: 634-637 (1973).

G.D. Syftestad & M.R. Urist, "Degradation of Bone Matrix Morphogenetic Activity by Pulverization," *Clin. Orthop. Rel. Res.* 141: 281-286 (1979).

M.R. Urist, "The Search for the Discovery of Bone Morphogenetic Protein (BMP)," *In Bone Grafts, Derivatives, and Substitutes* (M.R. Urist, B.T. O'Conner & R.G. Burwell, eds.

M. Muthukumaran et al., "Dose-Dependence of an Threshold for Optimal Bone Induction by Collagenous Bone Matrix and Osteogenin-Enriched Fraction," *Col. Rel. Res.* 8: 433-441.

R.G. Hammonds, Jr. et al., Bone-Inducing Activity of Mature BMP-2b Produced from a Hybrid BMP-2a/2b Precursor,*Mol. Endocrinol.* 5: 149-155 (1991).

U. Ripamonti et al., "The Critical Role of Geometry of Porous Hydroxyapatite Delivery System in Induction of Bone by Osteogenin, a Bone Morphogenetic Protein," *Matrix* 12: 202-212.

U. Ripamonti et al., "Induction of Bone in Composites of Osteogenin and Porous Hydroxyapatite in Baboons." Plast. Reconstr. Surg. 89: 731-739 (1992).

M.R. Urist et al., Neutral Lipids Facilitate Transfer of Bone Morphogenetic Protein s and Other Noncollagenous Proteins, *Med. Hypotheses* 49: 465-475 (1997).

M.R. Urist, "Bone Formation by Autoinduction," *Science* 150: 893-899 (1965).

E. Maddox et al., "Optimizing Human Demineralized Bone Matrix for Clinical Application," *Tissue Engineer.* 6: 441-448 (2000).

R.R. Wuthier & E.D. Eanes, "Effect of Phospholipids on the Transformation of Amorphous Calcium Phosphate to Hydroxyapatite in Vitro," *Calcif. Tissue Res.* 19: 197-210 (1975).

M.E. Nimni et al., "The Effect of Aging on Bone Formation in Rats: Biochemical and Histological Evidence for Decreased Bone Formation Capacity," *Calcif. Tissue Int.* 37: 617-624.

K.A. Fitzgerald et al., *The Cytokine Facts Book* (2d ed., Academic Press, San Diego, 2001), pp. 35-126.

F.P. Luyten et al., "Purification and Partial Amino Acid Sequence of Osteogenin, a Protein Initiating Bone Differentiation," *J. Biol. Chem.* 264: 13377-13380 (1989).

E. Ozkaynak et al., "Murine Osteogenic Protein (OP-1): High Levels of mRNA in Kidney," *Biochem. Biophys. Res. Commun.* 179: 116-123 (1991).

R.M. Harland et al., "The Transforming Growth Factor β Family and Induction of the Vertebrate Mesoderm: Bone Morphogenetic Proteins are Ventral Inducers," *Proc. Natl. Acad. Sci.*

S.K. Maiti & G.R. Singh, "Bone Morphogenetic Proteins-Novel Regulators of Bone Formation," *Ind. J. Exp. Biol.* 36: 237-244 (1998).

J.M. Wozney et al., "Novel Regulators of Bone Formation: Molecular Clones and Activities," Science 242: 1528-1534 (1988).

D.M. Kingsley et al., "What Do BMPs Do in Mammals? Clues from the Mouse Short-Ear Mutation," *Trends Genet.* 10: 16-21 (1994).

C. Scheufler et al., "Crystal Structure of Human Bone Morphogenetic Protein-2 at 2.7 A Resolution," *J. Mol. Biol.* 287: 103-115 (1999).

J.Q. Feng et al., "Structure and Sequence of Mouse Bone Morphogenetic Protein-2 Gene (BMP-2): Comparison of the Structures and Promoter Regions of BMP-2 and BMP-4 Genes," *Biochim.*

N. Ghosh-Choudhury et al., "Expression of the BMP 2 Gene During Bone Cell Differentiation," *Crit. Rev. Eukaryot. Gene Expr.* 4: 345-355 (1994).

B.L. Rosenzweig et al., "Cloning and Characterization of a Human Type II Receptor for Bone Morphogenetic Proteins." Proc. Natl. Acad. Sci. USA 92: 7632-7636.

L.J. Jonk et al., "Identification and Functional Characterization of a Smad Binding Element (SBE) in the JunB Promoter That Acts as a Transforming Growth Factor-β, Activin, and Bone-Morphogenetic-Protein-Inducible Enhancer," *J. Biol. Chem.* 273: 21145-21152 (1998).

M. Kawabata et al., "Signal Transduction by Bone Morphogenetic Proteins," *Cytokine Growth Factor Rev.* 9: 49-61 (1998).

P.K. Bajpai & W.G. Billotte, "Ceramic Biomaterials" *In* The *Biomedical Engineering Handbook* (J.D. Bronzino, ed., CRC Press, Boca Raton, FL, 1995), ch. 41, pp. 552-580.

M. Nimni et al., "Ostogenesis in Bone Defects in Rats: The Effects of Hydroxyapatite and Demineralized Bone Matrix," Am. J. Med. Sci. 298: 371-376 (1989).

\* cited by examiner

BONE GRAFT MATERIAL INCORPORATING DEMINERALIZED BONE MATRIX AND LIPIDS

CROSS-REFERENCES

This application is a continuation-in-part application of application Ser. No. 09/950,264 by Marcel E. Nimni, filed on Sep. 10, 2001 now U.S. Pat. No. 6,565,884 and entitled "Bone Graft Material Incorporating Demineralized Bone Matrix and Lipids," which is incorporated herein in its entirety by this reference.

BACKGROUND OF THE INVENTION

Field of the Invention

General Background and State of the Art

This invention is directed to a bone graft material incorporating demineralized bone matrix and lipids for particular use in enhancing bone formation.

One of the few tissues that regenerates in mammals is bone. To a great extent, this is due to the ability of specific growth factors to stimulate stem cells along the chondrogenic and osteogenic pathways and the role of mechanical forces that encourage bone remodeling.

Significant efforts have been made to enhance bone healing using decalcified bone matrix as an inducer. Decalcified bone matrix, which is mostly collagen with small amounts of growth- and differentiation-inducing molecules, is able to stimulate bone formation, even after implantation (subcutaneously or intramuscularly) at ectopic sites where there is no bone. The chondro-osteogenic response induced by implants of demineralized rabbit (M. R. Urist & T. A. Dowell, "The Inductive Substratum for Osteogenesis in Pellets of Particulate Bone Matrix," *Clin. Orthoped. Rel. Res.* 61:61-68 (1969); M. R. Urist & B. S. Strates, "Bone Morphogenetic Protein," *J. Dent. Res.* 50:1392-1406 (1971)) and rat bone matrix (C. B. Huggins et al., "Transformation of Fibroblasts by Allogeneic and Xenogeneic Transplants of Demineralized Tooth and Bone," *J. Exp. Med.* 132:1250-1258 (1970); A. H. Reddi & C. B. Huggins, "Influence of Transplanted Tooth and Bone on Transformation of Fibroblasts," *Proc. Soc. Exp. Biol. Med.* 143:634-637 (1973); G. D. Syftestad & M. R. Urist, "Degradation of Bone Matrix Morphogenetic Activity by Pulverization," *Clin. Orthoped. Rel. Res.* 141:281-286 (1979)).

The data suggested that bone morphogenetic protein was associated with a relatively acid-resistant, trypsin labile, water-insoluble non-collagenous protein of previously uncharacterized nature (B. S. Strates & J. J. Tideman, "Contribution of Osteoinductive and Osteoconductive Properties of Demineralized Bone Matrix to Skeletal Repair," *Euro. J. Exp. Musculoskel. Res.* 2:61-67 (1993); M. R. Urist et al., "Solubilized and Insolubilized Bone Morphogenetic Protein," *Proc. Natl. Acad. Sci USA* 76:1828-1832 (1979). This has been followed by extensive work attempting to further purify factors with bone morphogenetic potential (M. R. Urist, "The Search for Discovery of Bone Morphogenetic Protein (BMP)," *In Bone Grafts, Derivatives and Substitutes* (M. R. Urist, B. T. O'Conner & R. G. Burwell, eds., Butterworth Heineman, London, 1994), pp. 315-362), and subsequently to generate a family of active recombinant bone BMP (i.e., morphogenetic proteins) molecules of human origin.

Acid (HCl)-demineralized bone matrix, which contains a mixture of BMPs, consistently induces formation of new bone with a quantity of powdered matrices in the 10-25 mg range, while less than 10 mg fails to induce bone formation. Bone matrix inactivated by extraction with guanidine hydrochloride, an efficient protein solublizing agent, restores bone-forming activity by the addition of the guanidine soluble proteins or partially purified BMP-3 (i.e., osteogenin), or recombinant BMP-2. Thus, new bone formation requires a combination of BMP and an insoluble collagenous substratum (M. Muthukumaran et al., "Dose-Dependence of and Threshold for Optimal Bone Induction by Collagenous Bone Matrix and Osteogenin-Enriched Fraction." *Col. Rel. Res.* 8:433-441 (1988); R. G. Hammonds, Jr. et al, "Bone-Inducing Activity of Mature BMP-2b Produced from a Hybrid BMP-2a/2b Precursor," *Mol. Endocrinol.* 5:149-155 (1991); U. Ripamonti et al., "The Critical Role of Geometry of Porous Hydroxyapatite Delivery System in Induction of Bone by Osteogenin, a Bone Morphogenetic Protein," *Matrix* 12:202-212 (1992); U. Ripamonti et al., "Induction of Bone in Composites of Osteogenin and Porous Hydroxyapatite in Baboons," *Plast. Reconstr. Surg.* 89:731-739 (1992)). The same preparation of guanidine extracted protein, partially purified bovine BMP-3 was inactive when implanted subcutaneously without an insoluble collagenous matrix, but when combined with collagen, induced bone formation.

Human demineralized bone is a powder. As such, it is difficult to use by the surgeon to fill bone defects or regenerate bone where it does not normally form. The DBM powder migrates intra-operatively and during the healing process. Mixing human DBM to a carrier can facilitate both intra-operative handling and biological healing.

Lipids were found to be present in very large amounts at various sites of normal bone formation (J. T. Irving & R. E. Wuthier, "Histochemistry and Biochemistry of Calcification with Special Reference to the Role of Lipids," *Clin. Orthoped. Rel. Res.* 56:237-260 (1968). Although there have been suggestions that the incidence and quantity of bone formation are greatest when BMP is combined with various biological synthetic materials (M. R. Urist et al., "Lipids Associated Closely with Bone Morphogenetic Protein (BMP) and Induced Heterotopic Bone Formation," *Connect. Tissue Res.* 36:9-20 (1997)), there is still a need for improved carriers for optimal results. There has been no suggestion that lecithin would serve as a suitable carrier. In work reported by Urist and coworkers (M. R. Urist et al., "Neutral Lipids Facilitate Transfer of Bone Morphogenetic Proteins and Other Noncollagenous Proteins," *Med. Hypotheses* 49:465-475 (1997)), composites of recombinant BMP-2 and acetone-soluble lipids were reported to induce larger deposits of bone than implants of recombinant BMP-2 without acetone soluble lipids. Acetone soluble lipids consisted chiefly of triglycerides, cholesterol, and saturated short chain fatty acids, and included little or no phospholipids.

There is particularly a need for an improved matrix for supplying the demineralized bone matrix that is easily moldable and biocompatible. There is a particular need for the development of compositions that can be varied in their physical form and consistency so that they can be made more solid or more liquid as the need requires.

There is also particularly a need for a composition that can be made in an extrudable form that is partially soluble in tissue fluids, such as is suitable for administration or delivery by a syringe. Such a composition should be compatible with other ingredients such as natural or artificial bone graft materials.

INVENTION SUMMARY

In general, a first embodiment of a demineralized bone putty composition according to the present invention comprises:
(1) demineralized bone matrix (DBM); and
(2) a lipid fraction selected from the group consisting of lecithin and a mixture of lecithin and triglycerides containing unsaturated fatty acids.

The mixture is such that the putty composition, in this embodiment, is moldable, biocompatible, slowly resorbable, insoluble in tissue fluid, and non-extrudable.

Typically, in this embodiment, the composition comprises about 30-40% of DBM (w/w) and about 60% of the lipid fraction.

In one alternative of this embodiment of the present invention, the lipid fraction comprises lecithin.

In another alternative of this embodiment of the present invention, the lipid fraction comprises a mixture of lecithin and triglycerides containing unsaturated fatty acids. Typically, when the composition contains a mixture of lecithin and triglycerides, the mixture of lecithin and triglycerides containing unsaturated fatty acids is about a 1:1 mixture.

In this alternative of the embodiment, the composition can further comprise a long-chain saturated fatty acid such as palmitic acid.

The DBM can be human DBM, rat DBM, or DBM from another animal such as a cow, a horse, a pig, a dog, a cat, a sheep, or another socially or economically important animal species. In one preferred alternative of this embodiment, the DBM is delipidated, such as by treatment with a chloroform-methanol mixture.

The composition can further comprise other ingredients. In one alternative, the composition can further comprise a calcium salt.

In another alternative, the composition can further comprise at least one antioxidant selected from the group consisting of Vitamin E and Vitamin C.

In still another alternative, the composition can further comprise an ingredient selected from the group consisting of methylcellulose and hydroxypropyl methylcellulose.

The lipid fraction of the composition can be sterilized by radiation using standard radiation sterilization techniques.

The composition can be formulated so that the phospholipids are solid or liquid at room temperature.

A second embodiment of the invention comprises a bone paste that contains an emulsion carrier, which can be aqueous or nonaqueous. Typically, the emulsion carrier is aqueous.

In general, this second embodiment of a composition according to the present invention comprises:
(1) about 15% to about 75% of an emulsion carrier;
(2) a bone-material-containing phase comprising:
  (a) demineralized bone matrix (DBM); and
  (b) an emulsifier component that is compatible with lipids.

The mixture is such that the composition is moldable, biocompatible, slowly resorbable, miscible with bone graft materials, soluble or partially soluble in tissue fluids, and extrudable.

Typically, the emulsion carrier is aqueous. However, the emulsion carrier can also be a nonaqueous polar solvent.

Typically, the composition comprises from about 15% to about 55% of the emulsion carrier, such as the aqueous phase. Preferably, the composition comprises from about 25% to about 45% of the emulsion carrier, such as the aqueous phase. More preferably, the composition comprises about 35% of the emulsion carrier, such as the aqueous phase.

The aqueous phase can be water, saline, or an electrolyte solution.

The emulsifier can be lecithin, alone or with triglycerides, as described above; another phospholipid; another anionic emulsifier; or a nonionic emulsifier.

This embodiment of the composition can further comprise other ingredients, such as a calcium salt or a long-chain saturated fatty acid such as palmitic acid.

This embodiment of a composition according to the present invention can further comprise an antibiotic or a growth factor. Alternatively, this embodiment can further comprise a platelet glue wound sealant comprising: (1) a plasma-buffy coat concentrate comprising plasma, platelets, and calcium; and (2) a fibrinogen activator in a concentration sufficient to initiate clot formation.

This embodiment of a composition can further comprise a preservative.

Another aspect of this embodiment of the invention is a composition that is a mixture of the bone paste composition plus another bone graft material. The additional bone graft material can be autograft bone graft material, allograft bone material, or artificial bone graft material such as coralline or another artificial bone graft material.

BRIEF DESCRIPTION OF THE DRAWINGS

The following invention will become better understood with reference to the specification, appended claims, and accompanying drawings, where:

DETAILED DESCRIPTION OF THE PREFERRED EMBODIMENTS

Figure 1:
FIG. 1 is a photomicrograph that shows new bone formation in the DBM/composite after 28 days implantation: (a) subcutaneously; and (b) intramuscularly.
Figure 1:
Figure 1:

One embodiment of the invention is an improved demineralized bone putty composition that meets these needs. In general, this embodiment of a demineralized bone putty composition according to the present invention comprises:
(1) demineralized bone matrix (DBM); and
(2) a lipid fraction selected from the group consisting of lecithin and a mixture of lecithin and triglycerides containing unsaturated fatty acids.

The mixture is such that the putty composition is moldable, biocompatible, slowly resorbable, insoluble in tissue fluid, and non-extrudable.

The composition can comprise from about 20% to about 80% of DBM and from about 80% to about 20% of the lipid fraction. Typically, the composition comprises about 30-40% of DBM and about 60% of the lipid fraction. Preferably, the composition comprises from about 35% to about 40% of DBM. Percentages recited for the DBM and lipid fraction are weight percentages unless indicated otherwise. In preparation of compositions according to the present invention, the DBM and lipid fraction can actually be dispensed by volume as long as the resulting weight percentages are as specified.

The preparation of demineralized bone matrix (DBM) is well understood in the art and is described, for example, in M. E. Nimni, "Polypeptide Growth Factors: Targeted Delivery Systems," *Biomaterials* 10:1201-1225 (1997), incorporated herein by this reference, and articles referenced therein. In general, DBM is prepared from cortical bone of various animal sources. It is purified by a variety of procedures for the removal of non-collagenous proteins and other antigenic determinants. It typically consists of more than 99% Type I collagen. The DBM can be, for example, human DBM or rat DBM; DBM from other species can alternatively be used. For example, the DBM can be DBM from another animal such as a cow, a horse, a pig, a dog, a cat, a sheep, or another socially or economically important animal species.

In one preferred alternative of this embodiment, as described in Example 1, the DBM is delipidated, such as by treatment with a mixture of chloroform and methanol. A particularly preferred mixture of chloroform and methanol is a 1:1 mixture of chloroform-methanol. Other solvents can alternatively be used for delipidation.

In one alternative of this embodiment of the present invention, the lipid fraction comprises lecithin.

In another alternative of this embodiment of the present invention, the lipid fraction comprises a mixture of lecithin and triglycerides containing unsaturated fatty acids. Typically, when the composition contains a mixture of lecithin and triglycerides, the mixture of lecithin and triglycerides containing unsaturated fatty acids is about a 1:1 mixture.

Lecithin is also known as phosphatidyl choline. Preferably, the fatty acids in lecithin suitable for use in preparations according to the present invention have chain lengths of 16 to 18 carbon atoms. Less preferably, fatty acids having other chain lengths can be used. Additionally, other phospholipids such as phosphatidyl ethanolamine can be substituted for phosphatidyl choline. However, phosphatidyl choline (lecithin) is typically preferred. The use of lecithin enhances the osteoinductivity of DBM as well as providing better handling properties.

A particularly suitable source of unsaturated fatty acids is corn oil. However, other vegetable oils containing high proportions of unsaturated fatty acids can alternatively be used.

Corn oil comprises approximately 15% saturated fatty acids. The remainder, approximately 85% of the fatty acids, are unsaturated: 25% mono-unsaturated, mostly oleic acid; 59% di-unsaturated, mostly linoleic acid; about 1% of fatty acids with higher degrees of unsaturation, mostly linolenic acid.

As indicated below, the lipid portion can further contain long chain saturated fatty acids such as palmitic acid (hexadecanoic acid). Other long-chain fatty acids can be used in place of or in addition to palmitic acid.

The lipid portion of the preferred composition of this embodiment contains lecithin combined with mixed triglycerides present in corn oil. The relative proportions of the lecithin and the mixed triglycerides can be varied depending on the fluidity or other physical properties desired. For example, and without limitation, the proportions can be 80:20, 60:40, or 65:35. Other proportions can be used. For mixing with hydroxypropyl methylcellulose, 80:20 is preferred.

In another preferred alternative of this embodiment, the lipid, portion can comprise 25% of a lipid preparation that is designated 90G and 75% of a lipid preparation that is designated 53MCT. The lipid preparation that is designated 90G is more than 90% lecithin. The lipid preparation that is designated 53MCT is approximately 53% lecithin with the remainder being medium chain triglycerides.

Other lipid fractions can be used.

The composition can further comprise other ingredients. In one alternative of this embodiment, the composition can further comprise a calcium salt. The proportion of the calcium salt can be from about 0.1% to about 2%. More preferably, the proportion of the calcium salt is from about 0.5% to about 2%. The calcium salt can be $CaCO_2$ or $Ca_3(PO_4)_2$. However, other calcium salts can be used.

The composition can further comprise at least one antioxidant selected from the group consisting of Vitamin E and Vitamin C.

The antioxidant can be Vitamin E. A suitable Vitamin E is tocopherol, such as a-tocopherol. A suitable preparation of a-tocopherol is mixed isomers from natural sources. Vitamin E can comprise from about 0.01% to about 1.0% of the composition. Preferably, if present, Vitamin E comprises about 0.10% of the composition.

The antioxidant can be Vitamin C. A suitable preparation of Vitamin C is ascorbic acid or a long-chain fatty acid ester of ascorbic acid such as ascorbyl palmitate, ascorbyl stearate, or ascorbyl myristate. Vitamin C can comprise from about 0.01% to about 2% of the composition. Typically, if present, Vitamin C comprises from about 0.1% to about 0.5% of the composition. Preferably, if present, Vitamin C comprises about 0.2% of the composition.

The composition can further comprise an ingredient selected from the group consisting of methylcellulose and hydroxypropyl methylcellulose.

The lipid fraction of the composition can be sterilized by radiation using standard radiation sterilization techniques, such as gamma radiation or electron beam radiation.

The key ingredients for bone to form include the availability of a calcifiable matrix, and the subsequent deposition of calcium and phosphate ion in its interstices to form a rigid composite.

The growth factors described above stimulate the synthesis of such osteoid by cells that reside in the environment. The addition of phosphate in the form of lecithin and calcium in the form of calcium carbonate or other calcium salts provide the ingredients to enhance a mineralization of the previously formed osteoid. The resultant free phosphate ions, and the solubilized forms of calcium, are then able to nucleate around the new collagen to generate the characteristic bone material, hydroxyapatite.

Both these ions, phosphate and calcium, are normally present at sites of calcification, where they are concentrated by specific biological processes. The vehicle-carrier used in this invention, at the same time that it provides a moldable vehicle for delivery, provides additional amounts of those ingredients necessary for bones to form.

Lecithin (phosphatidyl choline) is a natural material widely used in the food and pharmaceutical industries. Its amphipathic properties endow it with compatibility toward lipids and water-soluble compounds, and is therefore useful for emulsifying fatty substances. In this connection it is used in manufacturing liposomes, or dispersions of lipid-soluble materials as droplets in water.

This property seems to significantly enhance the ability of the hydrophobic growth factors present in DBM to exert their functions, to stabilize such molecules, and to delay their biodegradation. It also provides a very suitable carrier which enables the user to apply the DBM at sites in the body where it is desirable that it should be retained, such as sites of fractures or bony defects.

Such mixtures, which have a putty or visco-fluid consistency allow the DBM particles to remain in place long enough for them to release their bioactive principles at the site of action. It is well established that in the absence of suitable carriers the BMPs are rapidly carried away by body fluids and are therefore useless.

The composition of this embodiment of the present invention is perfectly suited for the purpose of generating bone. The calcium ions released from the calcium carbonate and other calcium salt further delay the solubilization process by forming insoluble calcium salts with the available organic phosphate present in a lecithin molecule.

Addition of antioxidants, such as vitamin E (tocopherol) and vitamin C (ascorbic acid or ascorbic acid derivatives) act as adjuvants and protect lecithin from oxidation. This is particularly useful as it relates to the process of sterilization of the lipid fraction using gamma radiation or electron beam radiation, which can generate free radicals which can otherwise destabilize the molecular structure of lecithin by oxidation.

Compositions according to the present invention can be prepared either in a solid (putty) form or in a liquid injectable form. As detailed below, in a second embodiment of the present invention, the composition is in a liquid form that is extrudable and soluble or partially soluble in tissue fluids.

In one preferred embodiment in which the composition is a liquid paste for injection, the composition is suitable for injection through a large gauge needle from a syringe. In this preferred embodiment, DBM (30-40% w/w) was mixed with a lecithin preparation containing sufficient corn oil to allow the mixture to flow. In order to prevent the particles from settling, the consistency was enhanced (made less fluid) by the addition of palmitic acid (hexadecanoic acid). Usually a ratio of 1:5, that is approximately 20% of palmitic acid, melted by heating prior to mixing sufficed to generate a flowable suspension.

In another preferred alternative of the first embodiment of the present invention, the putty is more hydrophilic and therefore easier to blend with the liquid blood-containing milieu at the site of application. The composition had a lipid fraction that had a lecithin:triglyceride ratio of 80:20 with 40% of demineralized bone matrix (DBM). To this putty preparation, 4% w/w of hydroxypropyl methylcellulose (Methocel) was added along with a small volume of water in the following ratios: 1 g of putty (containing DBM and the lipid fraction), 40 mg of hydroxypropyl methylcellulose, and 0.2 ml of water. The mixture holds well, is cohesive at 37° C., and remains as such when placed in saline at 37° C.

The use of hydroxypropyl methylcellulose or similar hydrophilic polymers and their ability to swell in water and remain cohesive at 37° C. imparts an ability to the putty to interact more efficiently with blood, bone chips, or fragments which are present at the site of application, or when purposely mixed with small bony fragments to augment its volume and biocompatibility.

In a second embodiment of the present invention, the composition is extrudable and is soluble in tissue fluids. This second embodiment of the invention is more accurately described as a bone paste and includes an emulsion carrier. Typically, the emulsion carrier is an aqueous phase; however, alternatively, the emulsion carrier can be a polar but nonaqueous solvent. In general, this second embodiment of a demineralized bone paste composition according to the present invention comprises:

(1) about 15% to about 75% of an emulsion carrier; and
(2) a bone-material-containing phase comprising:
 (a) demineralized bone matrix (DBM); and
 (b) an emulsifier component that is compatible with lipids.

The mixture is such that the bone paste composition is moldable, biocompatible, slowly resorbable, miscible with bone graft materials, soluble or partially soluble in tissue fluids, and extrudable.

The bone paste composition provides slow release of active ingredients such as DBM. The composition also can undergo slow swelling, which modulates the rate of exposure of the growth factors in DBM to cells. The slow swelling can assist integration with blood and bone chips from an autologous graft. The use of carboxymethylcelluloses, as described above, can modulate this behavior. DBM can be retained within the composite.

Typically, the emulsion carrier is an aqueous phase. However, alternatively, the emulsion carrier can be a polar but nonaqueous solvent such as dimethylformamide (DMF), dimethylsulfoxide (DMSO), or acetonitrile.

Typically, the emulsion carrier, such as the aqueous phase, comprises from about 15% to about 55% of the composition. Preferably, the emulsion carrier, such as the aqueous phase, comprises from about 25% to 45% of the composition. More preferably, the emulsion carrier, such as the aqueous phase, comprises about 35% of the composition.

The aqueous phase can comprise water, normal saline, or an aqueous electrolyte solution.

In this embodiment, the bone-material-containing phase can comprise from about 20% to about 80% of DBM and from about 80% to about 20% of the emulsifier component. Typically, the bone-material-containing phase comprises about 30-40% of DBM and about 60% of the emulsifier component. Preferably, the bone-materialcontaining phase comprises from about 35% to about 40% of DBM. Percentages recited for the DBM and emulsifier component are weight percentages unless indicated otherwise. The composition can comprise from about 20% to about 80% of DBM and from about 80% to about 20% of the lipid fraction. Typically, the composition comprises about 30-40% of DBM and about 60% of the lipid fraction. Preferably, the composition comprises from about 35% to about 40% of DBM. Percentages recited for the DBM and lipid fraction are weight percentages unless indicated otherwise.

The DBM is prepared as described above. As described above, the DBM can be, for example, human DBM or rat DBM; DBM from other species can alternatively be used. For example, the DBM can be DBM from another animal such as a cow, a horse, a pig, a dog, a cat, a sheep, or another socially or economically important animal species.

The DBM can be delipidated as described above.

In one alternative of this embodiment of the present invention, the emulsifier component comprises lecithin, as described above. In another alternative of this embodiment, the emulsifier component comprises lecithin and triglycerides containing unsaturated fatty acids. When the emulsifier component comprises lecithin and triglycerides containing unsaturated fatty acids, the relative proportions of the lecithin and the triglycerides containing unsaturated fatty acids can be varied as described above. For example, without limitation, ratios of about 1:1 and about 64:36 are possible.

As described above, the unsaturated fatty acids can be from corn oil. When the unsaturated fatty acids are from corn oil, the ratio of lecithin and unsaturated fatty acids from corn oil can be about 20:80, about 40:60, or about 35:65; these alternatives are exemplary and are not by way of limitation. Other ratios are possible.

In another alternative of this embodiment, the emulsifier component can comprise at least one anionic emulsifier. The anionic emulsifier can be a phospholipid, such as phosphatidyl serine, phosphatidyl ethanolamine, phosphatidyl inositol, diphosphatidyl glycerol, or sphingomyelin. Other phospholipids can be used. Alternatively, the anionic emulsifier can be an emulsifier such as sodium lauryl sulfate, sodium laureth sulfate, sodium oleyl succinate, sodium dodecylbenzenesulfonate, dioctyl sodium sulfosuccinate, sodium stearoyl lactylate, or sodium isostearoyl lactylate.

Alternatively, the emulsifier can be a nonionic emulsifier. The nonionic emulsifier can be a synthetic emulsifier such as a glyceryl ester, a sorbitan fatty acid ester, a polyoxyethylene glycol ester, a polyethylene glycol ether, a polyoxyethylene derivative of a polyethylene glycol ether, a polyethyleneglycol ether of cetearyl alcohol, or a polyethylene glycol.

This embodiment of the composition can further comprise other ingredients. In one alternative of this embodiment, the composition can further comprise a calcium salt. The proportion of the calcium salt can be from about 0.1% to about 2%. More preferably, the proportion of the calcium salt is from about 0.5% to about 2%. The calcium salt can be $CaCO_3$ or $Ca_3(PO_4)_2$. However, other calcium salts can be used.

This embodiment of the composition can further comprise at least one antioxidant selected from the group consisting of Vitamin E and Vitamin C.

The antioxidant can be Vitamin E. A suitable Vitamin E is tocopherol, such as a-tocopherol. A suitable preparation of a-tocopherol is mixed isomers from natural sources. Vitamin E can comprise from about 0.01% to about 1.0% of this embodiment of the composition. Preferably, if present, Vitamin E comprises about 0.10% of this embodiment of the composition.

The antioxidant can be Vitamin C. A suitable preparation of Vitamin C is ascorbic acid or a long-chain fatty acid ester of ascorbic acid such as ascorbyl palmitate, ascorbyl stearate, or ascorbyl myristate. Vitamin C can comprise from about 0.01% to about 2% of the composition. Typically, if present, Vitamin C comprises from about 0.1% to about 0.5% of the composition. Preferably, if present, Vitamin C comprises about 0.2% of this embodiment of the composition.

This embodiment of the composition can further comprise at least one ingredient selected from the group consisting of methylcellulose, methylcellulose derivatives, carboxymethyl cellulose, and hydroxypropyl methylcellulose. These ingredients act as an emulsion stabilizer. They stabilize the lecithin emulsion and enhance its ability to incorporate blood, body fluids, and tissue particles into the emulsion. Preferably, the emulsion stabilizer is methylcellulose (methocell), carboxymethyl cellulose, or a methylcellulose derivative. Preferably, the methylcellulose, carboxymethylcellulose, or methylcellulose derivative comprises from about 0.1% to about 5% of the composition.

This embodiment of the composition can further comprise a long-chain saturated fatty acid. Typically, the long-chain saturated fatty acid is palmitic acid; however, other long-chain saturated fatty acids such as myristic acid and stearic acid can be used.

This embodiment of the composition can further comprise an antibiotic, typically incorporated in the aqueous phase. The antibiotic can be one or more of the following: tetracyclines, erythromycin, penicillins, methicillin, nafcillin, oxacillin, cloxacillin, dicloxacillin, ampicillin, amoxicillin, bacampicillin, carbenicillin, ticarcillin, mezlocillin, piperacillin, cephalosporins, gentamicin, tobramycin, amikacin, netilmycin, kanamycin, neomycin, clarithromycin, azithromycin, clindamycin, spectinomycin, vancomycin, and rifamycins. The use of other antibiotics is possible. The structures and uses of these and other antibiotics are disclosed in J. G. Hardman & L. G. Limbird, eds., *Goodman & Gilman's The Pharmacological Basis of Therapeutics* (9th ed., McGraw-Hill, New York, 1996), pp. 1073-1153, incorporated herein by this reference.

This embodiment of the composition can further comprise a growth factor, typically incorporated in the emulsion carrier such as the aqueous phase. The growth factor can be one or more of the following: an interleukin; a bone morphogenetic protein (BMP); brain-derived neurotrophic factor (BDNF); transforming growth factor $\alpha$(TGF$\alpha$); transforming growth factor $\beta_1$ (TGF$\beta_1$); transforming growth factor $\beta_2$ (TGF$\beta$); acidic fibroblast growth factor (aFGF); basic fibroblast growth factor (bFGF); granulocyte colony-stimulating factor (G-CSF); glial cell line-derived growth factor (GDNF); granulocyte/macrophage colony-stimulating factor (GM-CSF); growth hormone; haemoinfiltrate CC chemokine 1 (HCC-1); insulin-like growth factor I (IGF I); insulin-like growth factor II (IGF II); macrophage colony-stimulating factor (M-CSF); and stem cell factor (SCF). The use of other growth factors is possible.

These growth factors are described in general in K. A. Fitzgerald et al., *The Cytokine Facts Book* (2d ed., Academic Press, San Diego, 2001). Specifically, the interleukins include IL-1, IL-2, IL-3, IL-4, IL-5, IL-6, IL-7, IL-8, IL-9, IL-10, IL-11, IL12, IL-13, IL-14, IL-15, IL-16, IL-17, and IL-18. IL-1 exists in two forms, IL-1$\alpha$ and IL-1$\beta$. IL-1$\alpha$ has 159 amino acids in the mature form in human and 156 in mouse; IL-1$\beta$ has 153 amino acids in the mature form in human and 159 in mouse. IL-2 has 133 amino acids in the mature form in human and 149 in mouse. IL-3 has 133 amino acids in the mature form in human and 140 in mouse. IL-4 has 129 amino acids in the mature form in human and 120 in mouse. IL-5 has 115 amino acids in the mature form in human and 113 amino in mouse. IL-6 has 183 amino acids in the mature form in human and 187 in mouse. IL-7 has 152 amino acids in the mature form in human and 129 in mouse. IL-8 has 99 amino acids in the mature form in human. IL-9 has 126 amino acids in the mature form in human and 126 in mouse. IL-10 has 160 amino acids in the mature form in human and 160 in mouse. IL-11 has 178 amino acids in the mature form in human and 178 in mouse. IL-12 has 115 amino acids in the mature form in human and 113 amino in mouse. IL-13 has 112 amino acids in the mature form in human and 113 amino in mouse. IL-114 has 483 amino acids in the mature form in human. IL-15 has 113 amino acids in the mature form in human and 114 in mouse. IL-16 has 115 amino acids in the mature form in human and 113 amino in mouse. IL-17 has 132 amino acids in the mature form in human and 133 amino in mouse. IL-18 has 522 amino acids in the mature form in human and 519 in mouse.

The BMPs are described in further detail in the following publications: (1) F. P. Luyten et al., "Purification and Partial Amino Acid Sequence of Osteogenin, a Protein Initiating Bone Differentiation," *J. Biol. Chem.* 264: 13377-13380 (1989); (2) E. Ozkaynak et al., "Murine Osteogenic Protein (OP-1): High Levels of mRNA in Kidney," *Biochem. Biophys. Res. Commun.* 179: 116-123 (1991); (3) R. M. Harland et al., "The Transforming Growth Factor $\beta$ Family and Induction of the Vertebrate Mesoderm: Bone Morphogenetic Proteins are Ventral Inducers," *Proc. Natl. Acad. Sci. USA* 91: 10243-10246 (1994); (4) S. K. Maiti & G. R. Singh, "Bone Morphogenetic Proteins-Novel Regulators of Bone Formation," *Ind. J. Exp. Biol.* 36: 237-244 (1998); (5) J. M. Wozney et al., "Novel Regulators of Bone Formation: Molecular Clones and Activities," *Science* 242: 1528-1534 (1988); (6) D. M. Kingsley et al., "What Do BMPs Do in Mammals? Clues from the Mouse Short-Ear Mutation,"

*Trends Genet.* 10: 16-21 (1994); (7) C. Scheufler et al., "Crystal Structure of Human Bone Morphogenetic Protein-2 at 2.7 A Resolution," *J. Mol. Biol.* 287: 103-115 (1999); (8) J. Q. Feng et al., "Structure and Sequence of Mouse Bone Morphogenetic Protein-2 Gene (BMP-2): Comparison of the Structures and Promoter Regions of BMP-2 and BMP-4 Genes," *Biochim. Biophys. Acta* 1218: 221-224 (1994); (9) N. Ghosh-Choudhury et al., "Expression of the BMP 2 Gene During Bone Cell Differentiation," *Crit. Rev. Eukaryot. Gene Expr.* 4: 345-355 (1994); (10) B. L. Rosenzweig et al., "Cloning and Characterization of a Human Type II Receptor for Bone Morphogenetic Proteins," *Proc. Natl. Acad. Sci. USA* 92: 7632-7636; (11) L. J. Jonk et al., "Identification and Functional Characterization of a Smad Binding Element (SBE) in the JunB Promoter That Acts as a Transforming Growth Factor-β, Activin, and Bone-Morphogenetic-Protein-Inducible Enhancer," *J. Biol. Chem.* 273: 21145-21152 (1998); and (12) M. Kawabata et al., "Signal Transduction by Bone Morphogenetic Proteins," *Cytokine Growth Factor Rev.* 9: 49-61 (1998). The BMPs represent a family of proteins that initiate, promote, and maintain cartilage and bone morphogenesis, differentiation and regeneration in both the developing embryo and the adult. There are more than 30 known BMPs, of which 15 are found in mammals. BMPs belong to the transforming growth factor β (TGFβ) superfamily, which includes TGFβs, activins/inhibins, Mullerian-inhibiting substance (MIS) and glial cell line-derived neurotrophic factor. Comparison and alignment of the amino acid sequences of BMPs reveal that BMPs, except for BMP-1, share a common structural motif that is distinct from the structure of BMP-1. These BMPs include BMP-2, BMP-3, BMP-3b, BMP4, BMP-5, BMP-6, BMP-7, BMP-8, BMP-8B, GDF-3, GDF-5, GDF-6, GDF-7, GDF-8, GDF9, GDF-10, and nodal. In this specification, the term "BMP," without further qualification, is to be taken to include BMP-1; the term "BMP sharing a common structural motif is to be taken to include BMPs other than BMP-1. These BMPs sharing a common structural motif are disulfide-linked dimeric proteins. BMP-1 is not properly a BMP family member; rather it is a procollagen C proteinase related to *Drosophila* tolloid and which is postulated to regulate BMP activity through proteolysis of BMP antagonists/binding proteins.

BDNF has 119 amino acids in the mature form in both human and, mouse. It has 70% 3-sheet and is expressed as a tightly associated homodimer.

TGFα has 50 amino acids in the mature form in both human and rat. It is a small integral membrane protein.

TGFβ$_1$ has 112 amino acids in the mature form in humans; there is greater than 98% homology between the functional regions of human and mouse molecules.

TGFβ$_2$ also has 112 amino acids in the mature form in humans; there is again greater than 98% homology between the functional regions of human and mouse molecules.

The growth factor aFGF has 155 amino acids in the mature form in humans and in mice.

The growth factor bFGF has 155 amino acids in the mature form in humans and 154 amino acids in the mature form in mice. The growth factor bFGF is composed entirely of a β-sheet structure with a 3-fold repeat of a four-stranded antiparallel β-meander that forms a barrel-like structure with three loops.

G-CSF has 177 or 174 amino acids in the mature form in humans and 178 amino acids in the mature form in mice. The 177-amino-acid and 174-amino-acid forms in humans are alternatively spliced variants. G-CSF forms a four a-helical bundle structure.

GDNF has 134 amino acids in the mature form in humans and mice.

GM-CSF has 127 amino acids in the mature form in humans and 124 amino acids in the mature form in mice. The molecule comprises a two-stranded antiparallel β-sheet with an open bundle of four α-helices.

Growth hormone has 191 amino acids in the mature form in humans and 190 amino acids in the mature form in mice. The molecule forms a four α-helical bundle structure.

HCC-1 has 74 amino acids in the mature form in humans.

IGF I exists in two isoforms, IGF IA and IGF IB. Both consist of A and B domains, homologous to the A and B chains of insulin, connected by a C peptide and an eight-amino-acid extension at the C terminus termed the D domain. In humans and in mice, the IGF IA and IGF IB isoforms are both 70 amino acids in length in the mature form. IGF I has a three-dimensional structure similar to insulin.

IGF II has 67 amino acids in the mature form in both humans and mice. It also consists of A, B, C, and D domains. IGF II also has a three-dimensional structure similar to insulin.

M-CSF exists in three mature forms in humans, with 522, 406, and 224 amino acids respectively. In mice, the mature form of M-CSF has 519 amino acids. At least a portion of the structure of M-CSF comprises two bundles of four α-helices laid end to end.

SCF has 248 or 220 amino acids in the mature form in both humans and mice, existing in long and short membrane-bound forms after removal of the predicted signal peptide. The molecule exists as a noncovalently linked homodimer that contains extensive α-helical and β-pleated sheets.

These growth factors can exist in multiple forms, such as: (1) splicing variants produced from mRNAs generated by spicing from alternative sites; (2) variants produced by proteolysis, such as the cleavage of signal peptides or propeptides; (3) variants produced by the presence or lack of glycosylation, typically N-linked glycosylation; (4) naturally-occurring isoforms; (5) naturally-occurring mutations or allelic variants; and (6) artificial variants produced by genetic engineering in which one or more amino acids in the primary sequence are altered by techniques such as site-specific mutagenesis; such artificial variants are frequently designated muteins. In general, these multiple forms are within the scope of the present invention when they exist or can be produced for a particular growth factor.

Additionally, growth factors useful in compositions according to the present invention can be incorporated into fusion proteins. Examples of fusion proteins incorporating bone morphogenetic proteins are disclosed in U.S. Pat. No. 6,352,972 to Nimni et al., incorporated herein by this reference. In general, such fusion proteins are also within the scope of the present invention when they exist or can be generated. These fusion proteins can incorporate multiple domains or domains from more than one naturally-occurring growth factor. They can also incorporate elements such as reporter genes or detection tags. Therefore, the use of such fusion proteins incorporating growth factors, including but not limited to BMPs, is within the scope of the invention. The BMPs can be BMPs sharing a common structural motif and that are disulfide-linked dimeric proteins, such as, but not limited to, BMP-2, BMP-3, BMP-3b, BMP-4, BMP-5, BMP-6, BMP-7, BMP-8, BMP-8B, GDF-3, GDF-5, GDF-6, GDF-7, GDF-8, GDF-9, GDF-10, and nodal. A particularly preferred BMP for incorporation into a fusion protein is BMP-3.

This embodiment of the composition can further comprise a preservative in a quantity sufficient to retard bacterial growth. Preservatives are well known in the art and can include, but are not necessarily limited to, methylparaben, ethylparaben, propylparaben, butylparaben, benzyl alcohol., chlorphenesin, or diazolidinyl urea. Other preservatives can be used.

This embodiment of the composition can further comprise a platelet glue wound sealant comprising: (1) a plasma-buffy coat concentrate comprising plasma, platelets, and calcium; and (2) a fibrinogen activator in a concentration sufficient to initiate clot formation. Typically, the fibrinogen activator is thrombin or batroxobin. Such a platelet glue wound sealant is disclosed in U.S. Pat. No. 5,733,545 to Hood, III, incorporated herein by this reference. Preferably, the plasma-buffy coat concentrate comprises plasma that contains platelets at a concentration of at least $1.0\times10^9$ cells/ml and fibrinogen at a concentration of at least 5 mg/ml. More preferably, the platelet concentration is from about $1.0\times10^9$ cells/ml to about $2.5\times10^9$ cells/ml and the fibrinogen concentration is from about 5 to about 15 mg/ml. The plasma-buffy coat concentrate can additionally include leukocytes, preferably at a concentration of at least $3.0\times10^7$ cells/ml. More preferably, the leukocyte concentration is from about $3.0\times10^7$ cells/ml to about $6.0\times10^7$ cells/ml. Preferably, the leukocytes present in the plasma-buffy coat concentrate comprise from about 60% to about 70% lymphocytes, about 15% to about 25% monocytes, and about 5% to about 25% neutrophils.

In a preferred alternative of this embodiment, the bone paste composition is compatible with a suspension of autologous bone marrow, which provides autologous growth factors and mesenchymal stem cells.

Typically, the bone paste composition that is this embodiment of the invention has a viscosity and consistency that allows it to be delivered to the desired tissue site via a syringe, such as a typical Luer-Lock syringe that has had its tip slightly widened. The bone paste composition is blendable with other bone graft materials, such as autograft material, allograft material (from cadavers), or artificial bone such as ceramics like coralline porous calcium salt ceramics (e.g., Pro Osteon), aluminum calcium phosphate, plaster of paris, hydroxyapatite, tricalcium phosphate, ferric-calcium-phosphorous oxides, zinc-calcium-phosphorous oxides, and zinc sulfate-calcium-phosphorous oxides. These and other suitable bone graft materials are described in P. K. Bajpai & W. G. Billotte, "Ceramic Biomaterials" in The *Biomedical Engineering Handbook* (J. D. Bronzino, ed., CRC Press, Boca Raton, Fla., 1995), ch. 41, pp. 552-580, incorporated herein by this reference.

Accordingly, another aspect of this embodiment is a composition that is a mixture of the bone paste composition plus another bone graft material. The proportions of the bone paste composition and the other bone graft material can be varied as desired.

EXAMPLES

Example 1

Lecithin Enhances the Osteoinductivity of DBM

Introduction

Demineralized bone matrix (DBM), an osteoinductive bone graft material, is widely used for a variety of bone grafting applications. It is used alone or mixed with carriers to form gels, putties and sheets (M. R. Urist, *Science* 150:893 (1965); E. R. Maddox et al., *Tissue Engineer.* 6:441-448 (2000). Lecithin is a phospholipid present in cell membranes, and found in significant amounts in the bone calcification front (R. R. Wuthier, *Calcif. Tissue Res.* 19:197-210 (1975)). The work reported in this Example examined the importance of lipids in the osteoinductive phenomenon. It also assessed the osteoinductive potential of a putty-like grafting material consisting of lecithin and DBM. In order to separate the osteoinductivity from any osteoconductive effects, the test materials were implanted ectopically (subcutaneously and intramuscularly), as well as adjacent to the cranial bone of rats.

Materials and Methods

Materials and Reagents:
Lecithin (Phospholipon 90G, American Lecithin Company, Oxford, Conn.), is a purified phosphatidylcholine obtained from soybean.

Preparation of DBM/lecithin Conjugate:
Fresh bones were procured from 180-220 g Fisher 344 rats. The cortical shafts were cleaned with several rinses of phosphate buffered saline (PBS), and soaked in ethanol to partially remove lipids and cellular debris. After freeze-drying, they were further ground into particle sizes of 100-500 µM, and decalcified with 0.6 N HCl/1% Triton X-100. For complete delipidation, particles were further soaked in 1:1 chloroform-methanol at room temperature for 12 hours. The DBM generated by such a process was designated as dDBM. Human DBM (Allosource, Denver, Colo.) was also tested; however, it was subjected to this delipidation process. Rat or human DBM was blended with lecithin to generate pastes of various concentrations (DBM concentrations from 20% to 80%). Composites were packed into gelatin capsules (No. 3, Eli Lilly, Ind.) for implantation.

Animal Implantation: Twenty-seven Fisher 344 rats and 12 athymic homozygous rnu/rnu (nude) rats were anesthetized and implants placed subcutaneously (SQ), intramuscularly, and subcutaneously adjacent to their cranial bones. Each animal received either four subcutaneous implants or two intramuscular implants. Implants were recovered 28 days postoperatively, fixed, decalcified, embedded and stained with hematoxylin-eosin (H & E) and Alcian Blue.

Alkaline Phosphatase Assay: Alkaline phosphatase activity was determined as previously described (M. E. Nimni et al., *Calcif. Tissue Int.* 37:617 (1985)).

Results and Discussion

Properties of the DBM/Lecithin Composite: Lecithin mixed with the DBM particles gave rise to a composite with ointment-like consistency. It improved the handling properties of DBM which could be easily molded and fitted into irregularly shaped defects. The composite was insoluble in water and blood. When incubated at 37° C., the lecithin containing formulations maintained a solid state and did not liquefy. The lecithin appeared to resorb within 7-14 days.

Endochondral and Intramembranous Bone Formation Using Human DBM/lecithin Composite: Endochondral bone formation was observed in the DBM/lecithin implants placed in the anterior abdominal wall musculature or subcutaneously for 28 days. New bone formation, characterized by bone matrix with osteocytes, is shown bridging DBM particles together in the implants (FIG. 1). FIG. 1 shows new bone formation in the DBM/composite after 28 days implantation: (a) subcutaneously; and (b) intramuscularly. The bridging of bone particles together generated tighter spaces within the implants that become hematopoietic marrow spaces. The devitalized DBM particles were clearly identified as amorphous stained material with empty osteocytic lacunae. Above the cranial bone there was a marked stimulation of new bone formation beyond the confines of the cranial structure.

Figure 2:
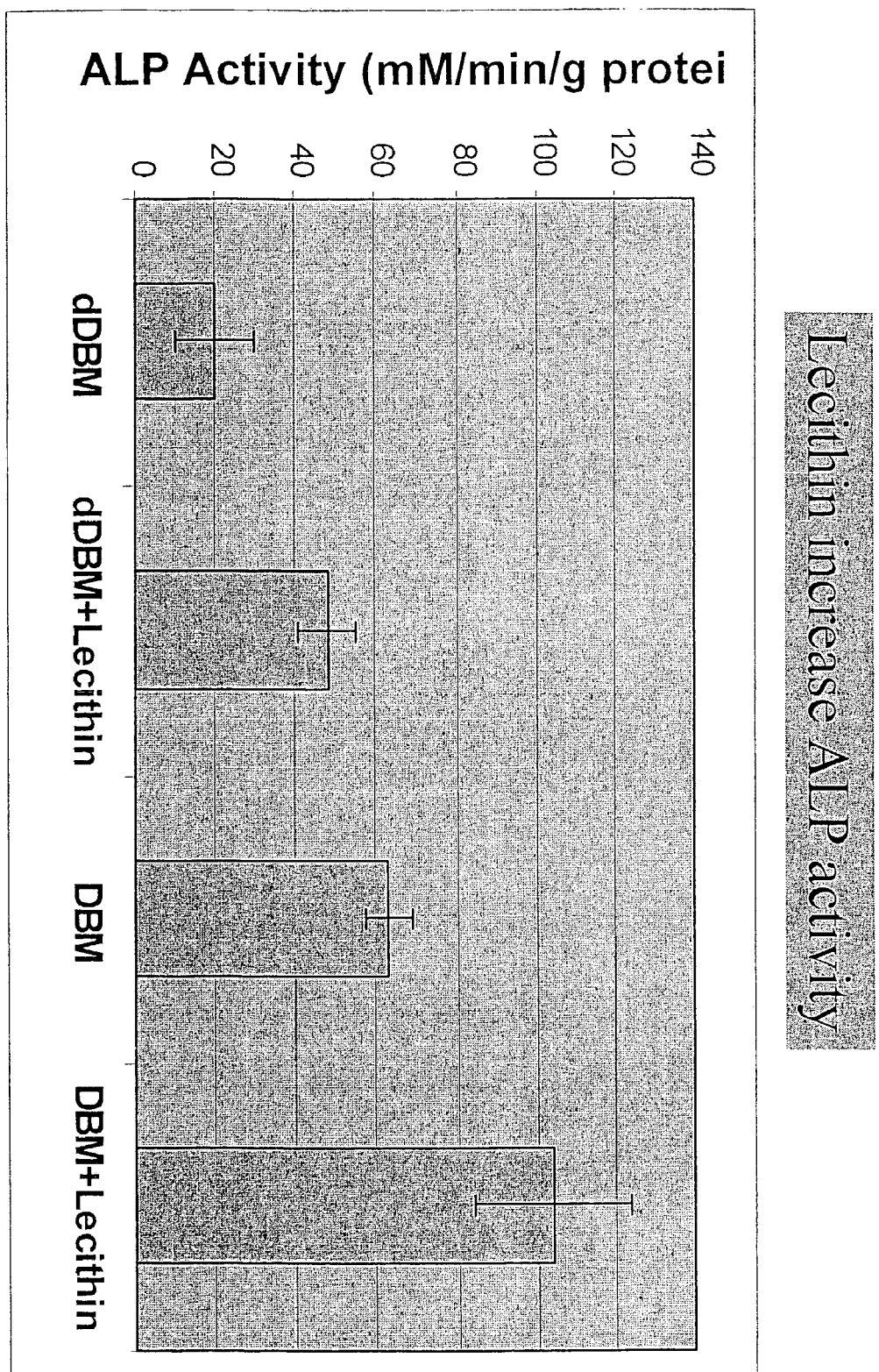
FIG. 2 is a graph showing the alkaline phosphatase (AP) activity (in mM/min/g protein) in 28-day postoperative explants with dDBM, dDBM/lecithin, DBM, and DBM/lecithin.

Lecithin Enhances Bone Formation:

Delipidizing with chloroform/methanol decreased bone formation compared to standard DBM containing lipids, but when phospholipids in the form of lecithin were added back, bone formation rates were significantly enhanced, above the levels stimulated by DBM alone. The histological results were always confirmed by alkaline phosphatase analysis of the explants (FIG. 2). FIG. 2 is a graph showing the alkaline phosphatase (AP) activity (in mM/min/g protein) in 28-day postoperative explants with dDBM, dDBM/lecithin, DBM, and DBM/lecithin.

Implantation of the composite superperiosteally in the cranial region caused further marked bone deposition.

Discussion

Lecithin is a relatively stable phospholipid present in significant amounts in the. calcification front. Composites containing DBM and lecithin appear to be practical for filling osseous defects particularly when there is concern of implant washout or migration. Recently, Urist (M. R. Urist et al., *Connect. Tissue Res.* 36:9-20 (1997) found that endogenous lipids are closely associated with BMP and facilitated heterotopic bone formation. If completely delipidized with chloroform/methanol during the process of preparation, the rate of ectopic bone formation by demineralized bone matrix was decreased by 80%. In the study reported in this Example, when lecithin was added back to delipidized DBM, obtained from rats or from a human bone bank (which includes a partial delipidizing step), bone formation and the closely correlated alkaline phosphatase activities increased.

In conclusion, lecithin blended with DBM not only provides better handling properties, but also has the ability to enhance the osteoinductivity of DBM.

ADVANTAGES OF THE INVENTION

Compositions according to the present invention deliver a biologically active product to animals or humans which can enhance bone formation in sites where bone is lost, deficient, or present in sub-optimal amounts. This composition generates a suitable moldable vehicle for retaining the active principles at the site of bone repair. It is compatible with other treatments to enhance bone growth or regeneration and is well tolerated by the organism to which it is administered. The composition can be prepared in a number of different physical forms depending on the need and the proposed route of administration. The use of lecithin not only provides better handling properties, but also enhances the osteoinductivity of DBM. In particular, the use of a bone paste containing an emulsion carrier, such as an aqueous phase, provides additional modes of administration and delivery and allows for the use of the composition in situations in which the use of an extrudable composition that is soluble or partially soluble in tissue fluids is desired.

While the specification describes particular embodiments of the present invention, those of ordinary skill can devise variations of the present invention without departing from the inventive concept.

I claim:

1. A demineralized bone paste composition comprising: (a) about 25% to about 75% of an emulsion carrier; and (b) a bone-material-containing phase comprising: (i) demineralized bone matrix (DBM); and (ii) an emulsifier component that is compatible with lipids; such that the paste is moldable, biocompatible, slowly resorbable, miscible with bone graft materials, soluble in tissue fluids, and extrudable; and wherein the emulsifier component comprises a mixture of lecithin and triglycerides containing unsaturated fatty acids.

2. The bone paste composition of claim 1 wherein the emulsion carrier comprises from about 15% to about 55% of the composition.

3. The bone paste composition of claim 2 wherein the emulsion carrier comprises from about 25% to about 45% of the composition.

4. The bone paste composition of claim 3 wherein the emulsion carrier comprises about 35% of the composition.

5. The bone paste composition of claim 1 wherein the emulsion carrier comprises an aqueous phase.

6. The bone paste composition of claim 1 wherein the emulsion carrier comprises a polar but nonaqueous solvent.

7. The bone paste composition of claim 6 wherein the polar but nonaqueous solvent is selected from the group consisting of dimethylformamide (DMF), dimethylsulfoxide (DMSO), and acetonitrile.

8. The bone paste composition of claim 5 wherein the aqueous phase comprises from about 15% to about 55% of the composition.

9. The bone paste composition of claim 8 wherein the aqueous phase comprises from about 25% to about 45% of the composition.

10. The bone paste composition of claim 9 wherein the aqueous phase comprises about 35% of the composition.

11. The bone paste composition of claim 5 wherein the aqueous phase comprises an aqueous liquid selected from the group consisting of water, saline, and an aqueous electrolyte.

12. The bone paste composition of claim 11 wherein the aqueous liquid is water.

13. The bone paste composition of claim 11 wherein the aqueous liquid is saline.

14. The bone paste composition of claim 11 wherein the aqueous liquid is an aqueous electrolyte.

15. The bone paste composition of claim 1 wherein the bone-material-containing phase comprises from about 20% to about 80% of DBM and from about 20% to about 80% of the emulsifier component.

16. The bone paste composition of claim 15 wherein the bone-material-containing phase comprises about 30% to about 40% of DBM.

17. The bone paste composition of claim 15 wherein the bone-material-containing phase comprises about 35% to about 40% of DBM.

18. The bone paste composition of claim 1 wherein the unsaturated fatty acids are about 25% mono-unsaturated fatty acids, about 59% di-unsaturated fatty acids, and about 1% of fatty acids with higher degrees of unsaturation, wherein the mono-unsaturated fatty acids comprise oleic acid, the di-unsaturated fatty acids comprise linoleic acid, and the fatty acids with higher degrees of unsaturation comprise linolenic acid.

19. The bone paste composition of claim 1 wherein the mixture of lecithin and triglycerides containing unsaturated fatty acids is about a 1:1 mixture.

20. The bone paste composition of claim 1 wherein the mixture of lecithin and triglycerides containing unsaturated fatty acids is about a 65:35 mixture.

21. The bone paste composition of claim 18 wherein the unsaturated fatty acids are from corn oil.

22. The bone paste composition of claim 21 wherein the lecithin and unsaturated fatty acids from corn oil is about 80:20.

23. The bone paste composition of claim 21 wherein the lecithin and unsaturated fatty acids from corn oil is about 60:40.

24. The bone paste composition of claim 21 wherein the ratio of lecithin and unsaturated fatty acids from corn oil is about 65:35.

25. The bone paste composition of claim 1 wherein the composition further comprises a calcium salt.

26. The bone paste composition of claim 25 wherein the calcium salt is from about 0.1% to about 2.0%.

27. The bone paste composition of claim 26 wherein the calcium salt is from about 0.5% to about 2.0%.

28. The bone paste composition of claim 25 wherein the calcium salt is selected from the group consisting of $CaCO_2$ and $Ca_3(PO4)_2$.

29. The bone paste composition of claim 28 wherein the calcium salt is $CaCO_2$.

30. The bone paste composition of claim 28 wherein the calcium salt is $Ca_3(PO4)_2$.

31. The bone paste composition of claim 1 wherein the composition further comprises at least one antioxidant selected from the group consisting of vitamin E and vitamin C.

32. The bone paste composition of claim 31 wherein the antioxidant is vitamin E.

33. The bone paste composition of claim 32 wherein the vitamin E is tocopherol.

34. The bone paste composition of claim 32 wherein the vitamin E comprises from about 0.01% to about 1.0% of the composition.

35. The bone paste composition of claim 34 wherein the vitamin E comprises about 0.1% of the composition.

36. The bone paste composition of claim 31 wherein the antioxidant is vitamin C.

37. The bone paste composition of claim 36 wherein the vitamin C comprises from about 0.01% to about 2.0% of the composition.

38. The bone paste composition of claim 37 wherein the vitamin C comprises from about 0.1% to about 0.5% of the composition.

39. The bone paste composition of claim 37 wherein the vitamin C comprises about 0.2% of the composition.

40. The bone paste composition of claim 1 wherein the composition further comprises at least one preservative in a quantity sufficient to retard bacterial growth.

41. The bone paste composition of claim 40 wherein the preservative is selected from the group consisting of methylparaben, ethylparaben, propylparaben, butylparaben, benzyl alcohol, chlorphenesin, and diazolidinyl urea.

42. The bone paste composition of claim 1 wherein the composition further comprises at least one ingredient selected from the group consisting of methylcellulose, carboxymethylcellulose, and hydroxypropyl methylcellulose.

43. The bone paste composition of claim 42 wherein the ingredient is methylcellulose.

44. The bone paste composition of claim 43 wherein the methylcellulose comprises from about 0.1% to about 5% of the composition.

45. The bone paste composition of claim 42 wherein the ingredient is carboxymethyl cellulose.

46. The bone paste composition of claim 45 wherein the carboxymethyl cellulose comprises from about 0.1% to about 5% of the composition.

47. The bone paste composition of claim 42 wherein the ingredient is hydroxypropyl methylcellulose.

48. The bone paste composition of claim 1 wherein the DBM is human DBM.

49. The bone paste composition of claim 1 wherein the DBM is rat DBM.

50. The bone paste composition of claim 1 wherein the DBM is DBM isolated from an animal species selected from the group consisting of cow, horse, pig, dog, cat, sheep, and another socially or economically important animal species.

51. The bone paste composition of claim 1 wherein the DBM is delipidated.

52. The bone paste composition of claim 51 wherein the delipidation is performed by treatment with a mixture of chloroform and methanol.

53. The bone paste composition of claim 1 wherein the composition further comprises a long-chain saturated fatty acid.

54. The bone paste composition of claim 53 wherein the long-chain saturated fatty acid is palmitic acid.

55. The bone paste composition of claim 1 wherein the lecithin is a phospholipid.

56. The bone paste composition of claim 55 wherein the phospholipid is selected from the group consisting of phosphatidyl seine, phosphatidyl ethanolamine, phosphatidyl inositol, diphosphatidyl glycerol, and sphingomyelin.

57. The bone paste composition of claim 1 wherein the composition further comprises an antibiotic in the aqueous phase.

58. The bone paste composition of claim 53 wherein the antibiotic is selected from the group consisting of tetracycline, erythromycin, penicillins, methicillin, nafcillin, oxacillin, cloxacillin, dicloxacillin, ampicillin, amoxicillin, bacampicillin, carbenicillin, ticarcillin, mezlocillin, piperacillin, cephalosporins, gentamicin, tobramycin, amikacin, netilmycin, kanamycin, neomycin, clarithromycin, azithromycin, clindamycin, spectinomycin, vancomycin, and rifamycins.

59. The bone paste composition of claim 1 wherein the composition further comprises a growth factor or a splice variant, a variant produced by proteolysis, a variant produced by the presence or lack of glycosylation, a naturally-occurring isoform, a naturally-occurring mutation or allelic variant, or a mutein of a growth factor.

60. The bone paste composition of claim 1 wherein the composition further comprises a growth factor.

61. The bone paste composition of claim 60 wherein the growth factor is selected from the group consisting of an interleukin, a bone morphogenetic protein (BMP), BDNF, TGFα1, TGFβ1, TGFβ2, aFGF, bFGF, G-CSF, GDNF, GM-CSF, growth hormone, HCC-1, IGF I, IGF II, M-CSF, and SCF.

62. The bone paste composition of claim 61 wherein the growth factor is a BMP.

63. The bone paste composition of claim 62 wherein the BMP is a BMP sharing a common structural motif and that is a disulfide-linked dimeric protein.

64. The bone paste composition of claim 63 wherein the BMP is selected from the group consisting of BMP-2, BMP-3, BMP-3b, BMP-4, BMP-5, BMP-6, BMP-7, BMP-8, BMP-8B, GDF-3, GDF-5, GDF-6, GDF-7, GDF-8, GDF-9, GDF-10, and nodal.

65. The bone paste composition of claim 64 wherein the BMP is BMP-3.

66. The bone paste composition of claim 1 wherein the composition further comprises a fusion protein that incorporates a growth factor.

67. The bone paste composition of claim 66 wherein the growth factor is a BMP.

68. The bone paste composition of claim 67 wherein the BMP is a BMP sharing a common structural motif and that is a disulfide-linked dimeric protein.

69. The bone paste composition of claim 68 wherein the BMP is selected from the group consisting of BMP-2, BMP-3, BMP-3b, BMP-4, BMP-5, BMP-6, BMP-7, BMP-8, BMP-8B, GDF-3, GDF-5, GDF-6, GDF-7, GDF-8, GDF-9, GDF-10, and nodal.

70. The bone paste composition of claim 69 wherein the BMP is BMP-3.

71. The bone paste composition of claim 1 wherein the composition further comprises a platelet glue wound sealant comprising: (i) a plasma-buffy coat concentrate comprising plasma, platelets, and calcium; and (ii) a fibrinogen activator in a concentration sufficient to initiate clot formation.

72. The bone paste composition of claim 71 wherein the fibrinogen activator is selected from the group consisting of thrombin and batroxobin.

73. The bone paste composition of claim 71 wherein the platelets are present at a concentration of at least about $1.0 \times 10^9$ cells/ml and the plasma-buffy coat concentrate contains fibrinogen at a concentration of at least about 5 mg/ml.

74. The bone paste composition of claim 73 wherein the platelets are present at a concentration of from about $1.0 \times 10^9$ cells/ml to about $2.5 \times 10^9$ cells/ml and the plasma-buffy coat concentrate contains fibrinogen at a concentration of from about 5 mg/ml to about 15 mg/ml.

75. The bone paste composition of claim 71 wherein the platelet glue wound sealant further comprises leukocytes.

76. The bone paste composition of claim 75 wherein the leukocytes are present at a concentration of at least $3.0 \times 10^7$ cells/ml.

77. The bone paste composition of claim 76 wherein the leukocytes are present at a concentration of from about $3.0 \times 10^7$ cells/ml to about $6.0 \times 10^7$ cells/ml.

78. The bone paste composition of claim 75 wherein the leukocytes comprise from about 60% to about 70% of lymphocytes, from about 15% to about 25% of monocytes, and from about 5% to about 25% of neutrophils.

79. The bone paste composition of claim 1 wherein the composition is compatible with a suspension of autologous bone marrow.

80. A composition comprising: (a) the demineralized bone paste composition of claim 1; and b) another bone graft material compatible and blendable with the demineralized bone paste composition.

81. The composition of claim 80 wherein the bone graft material is selected from the group consisting of autograft bone material, allograft bone material, and artificial bone graft material.

82. The composition of claim 81 wherein the bone graft material is autograft bone material.

83. The composition of claim 81 wherein the bone graft material is allograft bone material.

84. The composition of claim 81 wherein the bone graft material is artificial bone graft material.

85. The composition of claim 84 wherein the artificial bone graft material is selected from the group consisting of coralline calcium salt based porous ceramics, aluminum calcium phosphate, plaster of paris, hydroxyapatite, tricalcium phosphate, ferric-calcium-phosphorous oxides, zinc-calcium-phosphorous oxides, and zinc sulfate-calcium-phosphorous oxides.

86. The composition of claim 85 wherein the artificial bone graft material is coralline calcium salt based porous ceramics.

\* \* \* \* \*